United States Patent
Kato et al.

(10) Patent No.: US 10,288,561 B1
(45) Date of Patent: May 14, 2019

(54) GAS ANALYZER

(71) Applicant: Shimadzu Co., Kyoto (JP)

(72) Inventors: Rui Kato, Kyoto (JP); Hideaki Katsu, Kyoto (JP); Fumiaki Otera, Kyoto (JP)

(73) Assignee: Shimadzu Co., Kyoto (JP)

( * ) Notice: Subject to any disclaimer, the term of this patent is extended or adjusted under 35 U.S.C. 154(b) by 0 days.

(21) Appl. No.: 15/933,393

(22) Filed: Mar. 23, 2018

(51) Int. Cl.
*G01N 21/00* (2006.01)
*G01N 21/39* (2006.01)
*G01N 21/3504* (2014.01)

(52) U.S. Cl.
CPC ......... *G01N 21/39* (2013.01); *G01N 21/3504* (2013.01); *G01N 2021/399* (2013.01)

(58) Field of Classification Search
CPC .. G01N 21/39; G01N 21/3504; G01N 21/031; G01N 2021/399; G01J 3/42
USPC .......................................................... 356/447
See application file for complete search history.

(56) References Cited

U.S. PATENT DOCUMENTS

| | | | | |
|---|---|---|---|---|
| 5,770,156 A * | 6/1998 | Dosoretz | ................ | G01N 21/03 356/434 |
| 5,876,674 A * | 3/1999 | Dosoretz | ................ | G01N 21/03 356/246 |
| 6,356,350 B1 * | 3/2002 | Silver | ................... | G01J 3/4338 250/343 |
| 8,073,637 B2 * | 12/2011 | Cline | ........................ | G01J 3/02 702/28 |
| 10,107,751 B2 * | 10/2018 | Scherer | .................. | G01N 21/61 |
| 2012/0004861 A1 * | 1/2012 | Cline | ........................ | G01J 3/02 702/24 |
| 2016/0150968 A1 * | 6/2016 | Imai | ..................... | A61B 5/0095 600/407 |
| 2017/0315051 A1 * | 11/2017 | Nagase | .................. | C23C 16/52 |

* cited by examiner

*Primary Examiner* — Md M Rahman
(74) *Attorney, Agent, or Firm* — Chris Mizumoto

(57) ABSTRACT

A gas analyzer is provided, capable of measuring specific gas amount information within a measurement target gas in which pressure varies greatly. The gas analyzer includes a calculation member for calculating specific gas amount information of the nth cycle, a gas pressure change amount calculation unit for calculating an amount of gas pressure change at each time, and a correction signal creation member for generating a time changing, corrected light intensity at each wavelength ν, by performing a fitting process using the time-changing intensity over a long time period in a time zone in which the amount of gas pressure change is small but using the time-changing intensity over a short time period in a time zone in which the amount of gas pressure change is large. The calculation member generates a light intensity change of the measurement light in the predetermined wavelength range of ν1 to ν2 of the nth cycle by using the time changing, corrected light intensity at each wavelength ν, and calculates the specified gas amount information for the nth cycle.

4 Claims, 4 Drawing Sheets

GAS ANALYZER

FIELD OF THE INVENTION

The present invention is related to a gas analyzer that uses a laser absorption spectroscopic method to detect a specific amount of gas information (density/partial pressure/concentration), and more particularly to a gas analyzer for measuring a specific amount of gas information in a vacuum region of a semiconductor manufacturing apparatus, in a heat treatment furnace, in a flue, in a processing furnace, in a target gas (intake and exhaust) of an internal combustion engine (engine), in a flow path of a fuel cell, or in a global warming gas, and so forth.

BACKGROUND OF THE INVENTION

As one method of measuring the oxygen concentration in a target gas for measurement, there is known an absorption spectrometry that uses the fact that oxygen molecules absorb light of only a specific wavelength region (for example, 761 nm). Because this absorption spectrometry is able to measure the target gas without contacting it, it is possible not only to measure the oxygen concentration in the target gas for measurement without disturbance but also to measure it in an extremely short response time.

Among absorption spectrometric methods, in particular, "wavelength tunable semiconductor laser absorption spectroscopy" that uses a wavelength tunable semiconductor laser (laser element) as a light source, is realized by a simple device configuration. For example, with regard to a gas analyzer using the "tunable semiconductor laser absorption spectroscopy," for a piping in which the target gas for measurement flows in a predetermined direction, it is common to add a wavelength tunable semiconductor laser and a light detection sensor (light receiving section) that are provided to face each other to form an optical path 1 (optical distance) across the piping through the incident optical window and the exiting window formed in the piping. (See, for example, Patent Document 1).

With such a gas analyzer, predetermined wavelength ν laser light (measurement light) is oscillated from the wavelength tunable semiconductor laser. The progress of the laser light is hindered by the shielding effect of the oxygen molecules present within the target gas for measurement in the course of passing through the pipe. Using the fact that the amount of light incident on the light detection sensor decreases in relation to the concentration of the oxygen molecules in the target gas, the concentration of the oxygen molecules is calculated by measuring the mount of the laser light I incident on the light detection sensor for the light amount of the laser light oscillated from the wavelength tunable semiconductor laser. FIG. 4 is a graph showing an example of an absorption spectrum obtained from the gas analyzer as described above. The vertical axis represents received light intensity I, and the horizontal axis represents wavelength ν. Note that $I_0(\nu)$ (reference line) is the received light intensity where the absorption of the oxygen molecules is not received at wavelength ν and is derived by creating an approximate expression based on the received light intensity I of the non-absorptive wavelength.

From Lambert-Beer's law, the following equation (1) holds.

$$\ln\left(\frac{I_0(\nu)}{I(\nu)}\right) = c \times l \times S(T) \times K(\nu) \quad (1)$$

$I_0(\nu)$ is the light intensity in the case of not receiving the absorption of oxygen molecules at wavelength ν, I(ν) is the transmitted light intensity at wavelength ν, c (mol/cm$^3$) is the number density of oxygen molecules, l (cm) is the length (optical distance) of the optical path through the target gas for measurement, S(T) (cm$^{-1}$/(mol/cm$^{-2}$)) is a function of temperature T at a given absorption line intensity, and K(ν) is the absorption profile function.

FIG. 5 shows a schematic diagram of an example of a gas analyzer using wavelength tunable semiconductor laser absorption spectroscopy. Note that the direction horizontal to the ground is defined as X direction, the direction perpendicular to the X direction that is horizontal to the ground is the Y direction, and the direction perpendicular to both the X direction and the Y direction is the Z direction.

A gas analyzer 101 includes a light source unit 10, a light receiving unit 20, a gas temperature sensor (not shown), and a control unit 140 constituted by a microcomputer or a PC.

The gas analyzer 101 is provided to measure an oxygen concentration Cn within a measurement target gas flowing in a sample flow passage 70 that connects to each line of supply and exhaust of the fuel cell system. The sample flow path 70 extends in the Z direction, and on the side wall of the sample flow path 70, there are formed a lens 35 serving as an incident optical window and a lens 36 serving as an exit optical window disposed so as to face the lens 35 with a distance 1 apart in the −X direction. The measurement target gas flows in the sample flow path 70 in the Z direction.

The light source unit 10 has a semiconductor laser 11 (for example, a distributed feedback system for optical communication (DFB: distributed feedback) semiconductor laser diode and so forth), a lens 13, and a D/A converter 12. Further, the laser light from the semiconductor laser 11 is configured to pass through an optical fiber 33 and a lens 13 in the −X direction and travel from the lens 35 into the sample flow channel 70 to irradiate the measurement target gas provided in the sample flow path 70.

Furthermore, the light source unit 10 of this type converts a drive current value for application to the semiconductor laser 11 by a predetermined cycle n; that is, specifically, by applying the drive current value of a saw-tooth shape, a laser beam having a predetermined wavelength range (sweep width) ν1 to ν2 is oscillated from the semiconductor laser 11 at a predetermined period n. FIGS. 6a and 6b represent conceptual diagrams showing a relationship between the drive current value and the oscillation wavelength ν of the laser light; that is, FIG. 6(a) is a waveform diagram of the drive current value for application to the semiconductor laser 11; and FIG. 6(b) is a wavelength diagram of the oscillation wavelength ν of the laser light oscillated from the semiconductor laser 11 to which the drive current value is applied.

The light receiving unit 20 may be any device as long as it can convert the light intensity I into an electric signal; for example, a photodiode 21 may be used. The photodiode 21 then is positioned to receive the laser light emitted in the −X direction outside the path 70 from the lens 36 via an optical fiber 34 and a lens 23 and receives the intensity I of the laser beam that has passed through the measurement target gas.

It is known that interference noise (fringe noise) is produced when different laser light traversing the optical distance 1 is reflected multiple times by the lenses 35, 36 and so forth and received by the photodiode 21. This interference noise cannot be completely eliminated even if low reflective materials are used for the lenses 35, 36, and so forth.

Therefore, by measuring only the interference noise with the photodiode 21 or extracting noise from the intensity I received from the photodiode 21 before measuring the oxygen concentration Cn and by subtracting in advance the measured or extracted interference noise from the received intensity I when measuring the oxygen concentration Cn, a corrected light intensity I from which the interference noise is removed can be created. Alternatively, by creating a light intensity as changed by time Iv(t) at a wavelength v, and by performing a fitting process using a signal (quadratic function) that matches the physical phenomenon for the time-changing Iv(t), a corrected light intensity, time-changing iv(t), from which the interference noise is removed can be made.

In each period n, the control unit 140 reads from the photodiode 21 through the A/D converter 22 the intensity $I_n(v1)$ to $I_n(v2)$ of the laser light and creates the corrected light intensity $i_n(v1)$ to $i_n(v2)$, and therefore, the oxygen concentration Cn can be calculated based on equation (1).

On the other hand, in the present automobile industry, there is a great demand to measure the hydrocarbon concentration and the like in exhaust gas from an internal combustion engine and the like. Therefore, it is conceivable that a gas analyzer 101 could be used to measure the density (specific gas amount information) Cn of oxygen molecules (specific gas) in the measurement target gas within a combustion chamber of an internal combustion engine.

PATENT DOCUMENT

[Patent Document 1] Japanese Patent Application Laid-Open No. 2010-237075

SUMMARY OF THE INVENTION

Problem to be Solved

It is known that the refractive index of a gas changes depending on temperature and density (pressure), but what is more dominant here is the density (pressure). Therefore, when measuring an oxygen concentration Cn of the target gas for measurement whose pressure P largely changes, the refractive index of the target gas greatly changes as well, and the optical path length l of the laser beam that passes through the measurement target gas also varies in proportion to the refractive index. As a result, the optical distance 1 of the laser beam passing through the measurement target gas changes because of the change in the pressure P, and interference noise is generated. At the same time, the transmittance and the absorption spectra of the measurement target gas also change according to the change in the pressure P.

Consequently, when the oxygen concentration Cn in the measurement target gas that greatly varies in pressure P is measured, the interference noise changes, and the parameters for fitting and noise filters cannot be predetermined, and all of these lead to difficulties in removing the interference noise from the intensity $I_n(v1)$ to $I_n(v2)$ of the acquired laser light.

The inventors have examined various methods of measuring the oxygen concentration Cn in the measurement target gas where the pressure P greatly changes. It was found that when the pressure change is large, the change in interference noise is fast, but, on the other hand, when the pressure change is small, the change in interference noise is slow. Therefore, for a time zone in which the amount of gas pressure change ΔP(t) is small, a fitting process is performed using the time-changing I(t) over a long time interval, but, on the other hand, for a time zone in which the amount of gas pressure change ΔP(t) is large, a fitting process is performed using the time-changing I(t) over a short time interval.

Effect of the Invention

That is, a gas analyzer of the present invention is a light source member for irradiating measurement light at predetermined time intervals in a predetermined wavelength range of v1 to v2 to a measurement target gas in a measurement object; a light receiving member for receiving a light intensity I of the measurement light having passed through the measurement target gas; a calculation member for calculating specific gas amount information in n cycles, using a light intensity change $I_n(v)$ of the measurement light in the predetermined wavelength range of v1 to v2 of the nth cycle; a pressure sensor for detecting a gas pressure P of the measurement target gas; a gas pressure change amount calculation member for generating a time change of P(t) of the gas pressure P and for calculating an amount of gas pressure change ΔP(t) at each time t; an acquisition signal generating member for generating a light intensity, time-changing $I_v(t)$, at each wavelength v; and a correction signal creation member for generating a corrected light intensity, time-changing $I_v(t)$, at each wavelength v, by performing a fitting process using the time-changing $I_v(t)$ over a long time interval in a time zone in which the amount of gas pressure change ΔP(t) is small but using the time-changing $I_v(t)$ over a short time interval in a time zone in which the amount of gas pressure change ΔP(t) is large, where the calculation member generates a light intensity change $i_n(v)$ of the measurement light in the predetermined wavelength range of v1 to v2 of the nth cycle by using the time-changing $i_v(t)$ of the corrected light intensity at each wavelength v, and calculates the specified gas amount information for the nth cycle.

"Predetermined time interval" means an arbitrary time interval (cycle) determined by an operator or the like; for example, in order to oscillate measuring light of a predetermined wavelength range, v1 to v2, from the laser element, several tens of Hz to several tens of kHz, more specifically 1 kHz and the like, are used. "Specific gas" is an arbitrary component determined by an operator or the like, and includes, for example, an acid, natural water vapor, carbon dioxide, carbon monoxide, and so forth.

According to the gas analyzer of the present invention as described above, it is possible to appropriately select the fitting range that relates to the periodic change due to the influence of the interference noise by using the amount of gas pressure change ΔP(t) for counting to set the fitting range. As a result, the specific gas amount information can be accurately calculated in the measurement target gas in which the pressure changes greatly.

Means and Effects for Solving Other Problems

In the above invention, the light source unit may include a laser element and a laser control unit for oscillating measurement light of a predetermined wavelength range of v1 to v2 at a predetermined cycle, n.

Further, in the above invention, the object for measurement may include an internal combustion engine for executing an intake process, a compression process, a combustion process, and an exhaust process in that order in a predetermined cycle. "Predetermined cycle" is an arbitrary time determined by an operator or the like, and this is longer than the predetermined time interval mentioned above.

DETAILED DESCRIPTION OF THE INVENTION

Hereinafter, embodiments and examples of the present invention will be described with reference to the drawings. It should be noted that the present invention is not limited to the embodiments and examples described below, and appropriate variations, modifications, and additions are included within the scope not deviating from the concept of the present invention.

Figure 1:
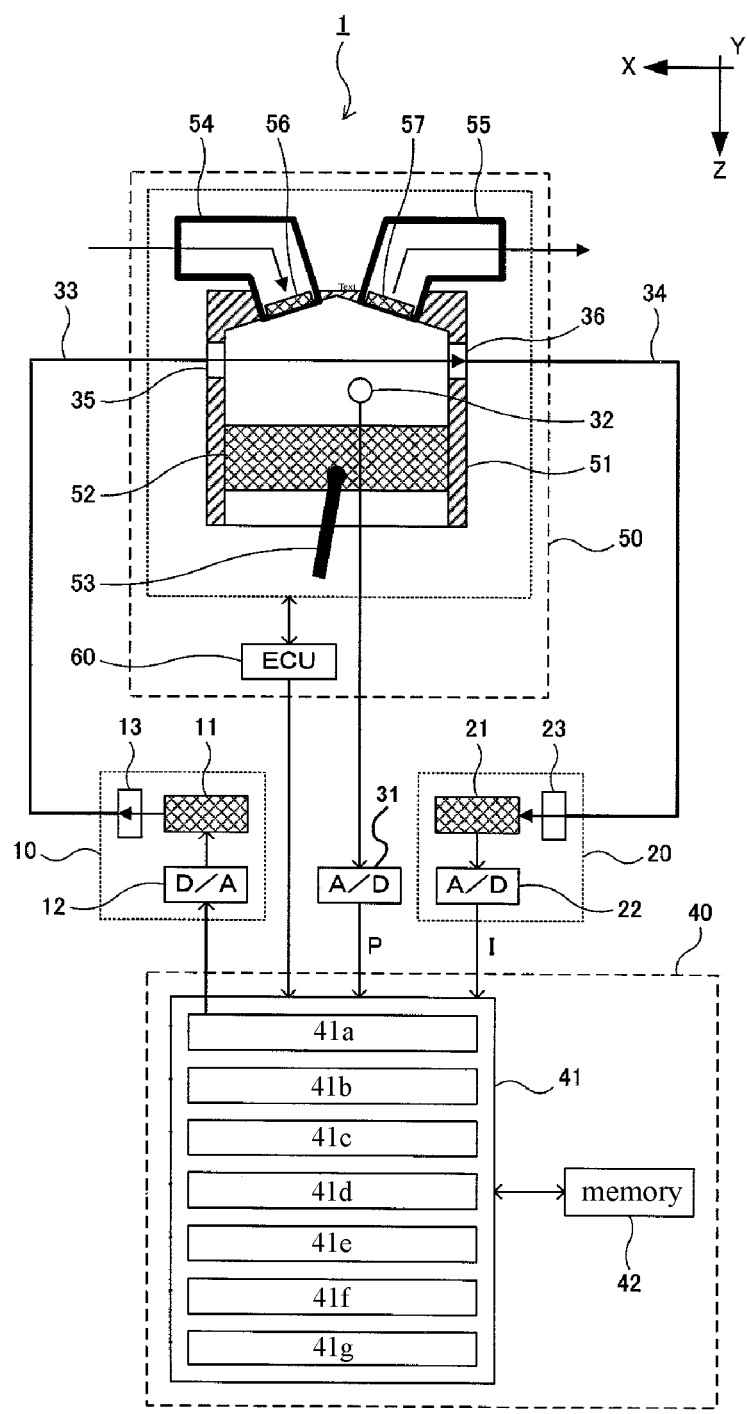
FIG. 1 is a schematic configuration drawing showing an embodiment of a gas analyzer of the present invention.

FIG. 1 is a schematic configuration drawing showing an embodiment of a gas analyzer of the present invention. The same reference numerals are given to the same components as those of the above-described conventional gas analyzer 101. The gas analyzer 1 includes a light source unit 10, a light receiving unit 20, a gas temperature sensor (not shown) for measuring temperature T, a pressure sensor 32 for measuring pressure P, and a control unit 40 in a microcomputer or a PC.

The gas analyzer 1 of the present invention is used for measuring a number density (specific gas quantity information), Cn, of oxygen molecules (specific gas) in the measurement target gas existing in the combustion chamber of an engine 50 (internal combustion engine). The engine 50 includes a cylinder 51, a piston 52 slidable in both the Z direction and the −Z direction in the cylinder 51, a crankshaft (not shown) connected to the piston 52 via a connecting rod 53, and an ECU 60 that controls the amount of fuel injection, ignition timing, and so forth.

The intake port and the exhaust port are formed in the head of the cylinder 51, and the intake port and the exhaust port communicate with the combustion chamber. The intake port is connected to an intake passage 54, and between the intake port and the combustion chamber, an intake valve 56 for opening and closing the intake port with respect to the combustion chamber is provided. The exhaust port is connected to an exhaust passage 55, and an exhaust valve 57 for opening and closing the exhaust port with respect to the combustion chamber is provided between the exhaust port and the combustion chamber. Although abbreviated, the combustion chamber is provided with an injector for injecting fuel into the combustion chamber and a spark plug for igniting an air-fuel mixture in the combustion chamber, and the like.

According to the engine 50, an intake process in which the intake gas from the intake passage 54 is drawn into the combustion chamber via the intake valve 56, is performed together with the descent of the piston 52. After the intake process, the intake valve 56 closes, and the piston 52 reaches the bottom dead center to raise the piston 52 so that the compression process is performed in which the fuel injected into the intake air is compressed in the combustion chamber. When the piston 52 rises to near the top dead center, the combustion process is performed by ignition against the air-fuel mixture at a predetermined timing. When the piston 52 descends because the combustion pressure rises again, the exhaust valve 57 is opened, and the exhaust process is performed in which the combustion gas in the combustion chamber is exhausted to the exhaust passage 55 as exhaust gas via the exhaust valve 57. A series of four processes—the intake process, the compression process, the combustion process, and the exhaust process—constitutes one cycle.

On the side wall of the cylinder 51, there are formed a lens 35 serving as an incident optical window and a lens 36 which is an exit optical window opposed to the lens 35 with a distance 1 in the −X direction.

Further, a pressure sensor 32 is installed in the combustion chamber and measures pressure P of the measurement target gas at predetermined time intervals and outputs it to the control unit 40 via the A/D converter 31.

The control unit 40 includes a CPU 41 and a memory 42 (data storage unit). Further, the function to be processed by the CPU 41 will be described in a block form. A laser control unit 41a controls the light source unit 10; a light intensity acquisition unit 41b acquires intensity I of the laser light; a pressure acquisition unit 41c acquires pressure P; a gas pressure change amount calculation unit 41d calculates an amount of gas pressure change ΔP(t); an acquired signal generation unit 41e generates a light intensity, time-changing Iv(t), at a wavelength v; a correction signal generation unit 41f generates a corrected light intensity, time-changing iv(t), at a wavelength v; and a calculation unit 41g calculates a number density Cn for the nth cycle.

The gas pressure change amount calculation unit 41d performs control to create time-changing P(t) of the gas pressure based on the pressure P acquired by the pressure acquisition unit 41c. Then, the gas pressure change amount calculation unit 41d performs control to calculate a gas pressure change ΔP(t) at each time t by differentiating the time changing P(t) of the gas pressure.

The acquired signal creation unit 41e performs control to create time-changing $I_v(t)$ of the light intensity at each wavelength v in a predetermined wavelength range of v1 to v2. For example, it creates time-changing LAO of the light intensity at the wavelength v1, time-changing $I_{vA}(t)$ of the light intensity at the wavelength vA, . . . , and time-changing $I_{v2}(t)$ of the light intensity at the wavelength v2, where v1<vA<v2.

Figure 2:
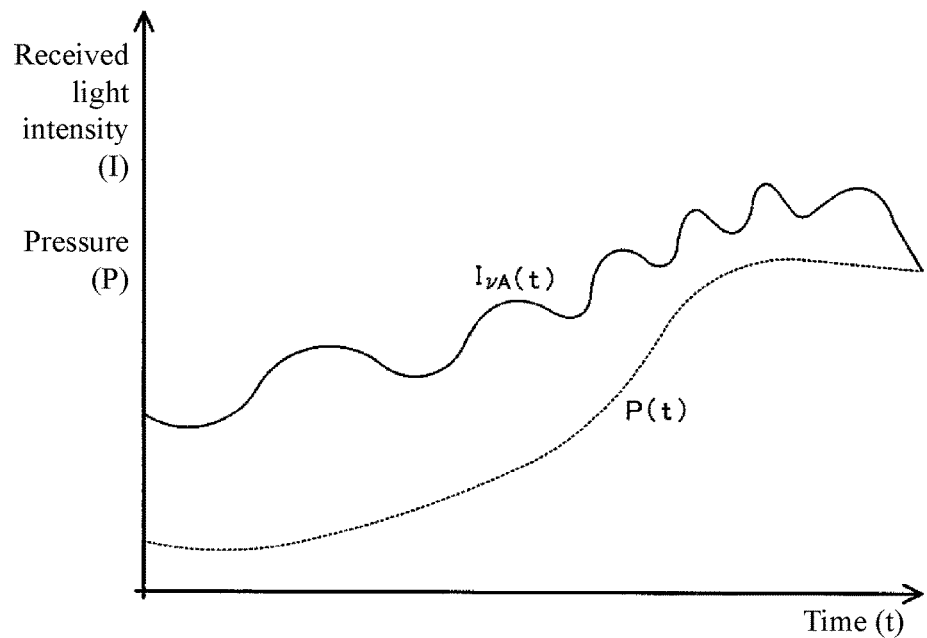
FIG. 2 is a graph showing an example of temporal changes in gas pressure and light intensity.

FIG. 2 shows an example of the time-changing P(t) of the gas pressure created by the gas pressure change amount calculation unit 41d and the time changing $I_v(t)$, of the light intensity created by the acquired signal generating unit 41e, shown in parallel. The time-changing $I_{vA}(t)$ of the light intensity at the wavelength vA is indicated by solid line, and the time-changing P(t) of the gas pressure is indicated by dotted line.

The correction signal generation unit 41f determines a fitting range W based on the amount of gas pressure change ΔP(t) at each time t and performs a fitting process using the time-changing $I_v(t)$ of the light intensity in the fitting range W to perform control to create a time-changing $i_v(t)$ of the corrected light intensity at each wavelength v. For example, by substituting the amount of gas pressure change ΔP(t) into the following equation (2), the fitting range W1 over the time zone t1 is determined, and then the fitting range W2 over the time zone t2 is determined, and in that manner, the fitting range W over each time zone is determined.

$$W=\alpha/(\Delta P(t))+\beta \qquad (2)$$

Here, α and β are constants.

With respect to the light intensity, the time-changing $I_{v1}(t)$, at the wavelength v1, a fitting process is performed using a quadratic function in the fitting range W1 over the time zone t1, and a fitting process is performed using a quadratic function in the fitting range W2 over the time zone t2 and in that manner, fitting process is performed using each quadratic function in each fitting range W over each time zone t. In this way, time-changing $i_{v1}(t)$ of the corrected light intensity is created.

Figure 3:
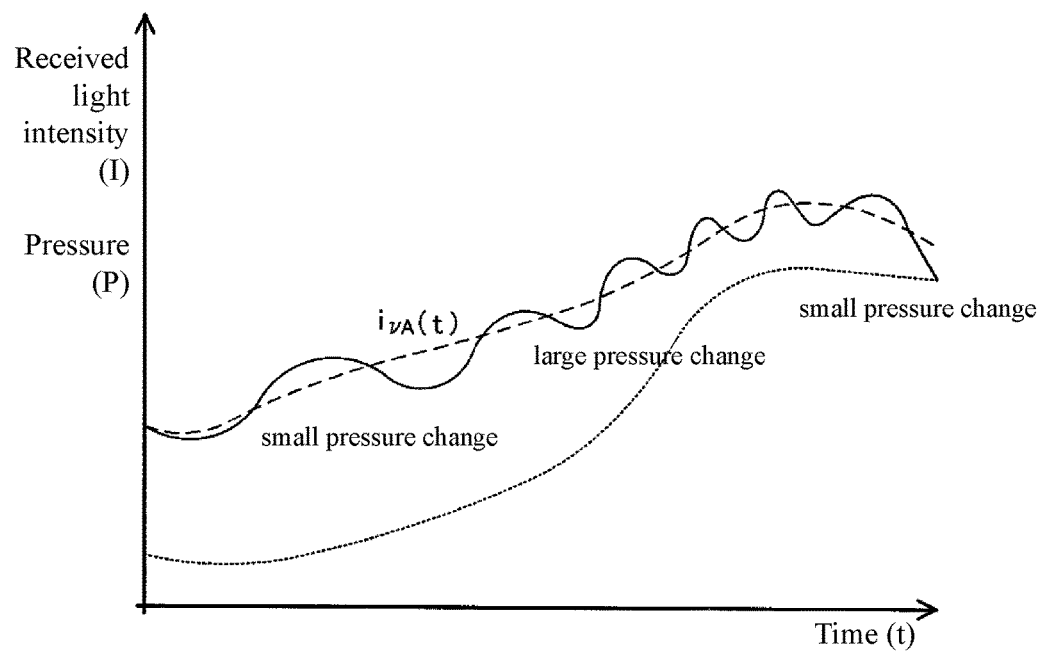
FIG. 3 is a graph showing an example of temporal change of the corrected light intensity superimposed on the graph of FIG. 2.
Figure 4:
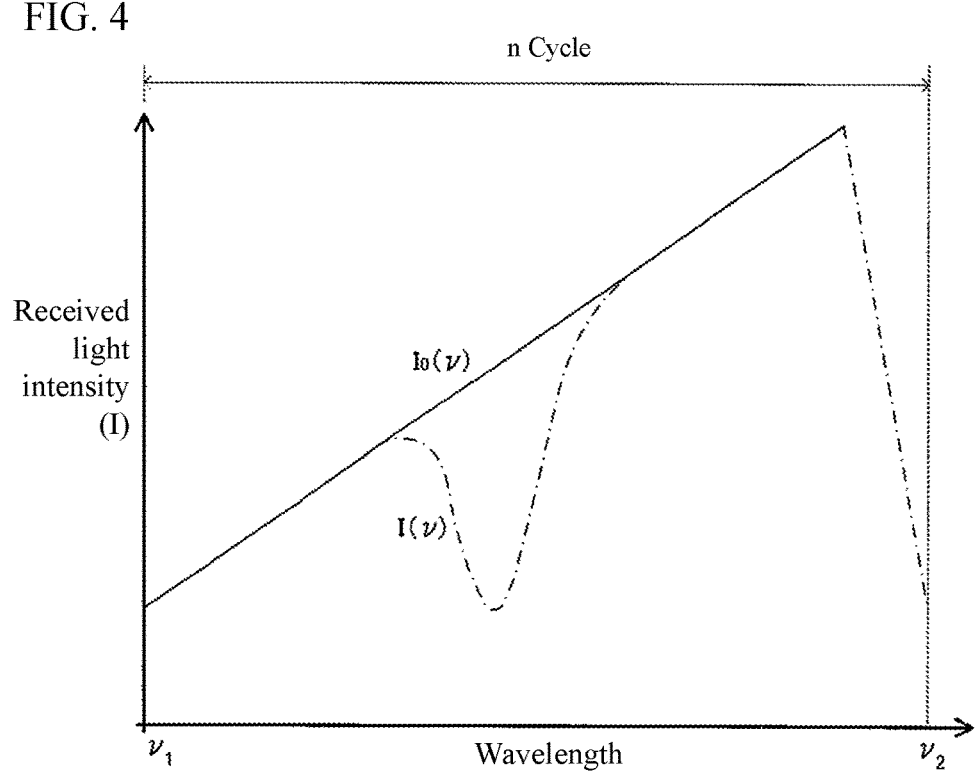
FIG. 4 is a graph showing an example of an absorption spectrum obtained by a conventional gas analyzer.
Figure 5:
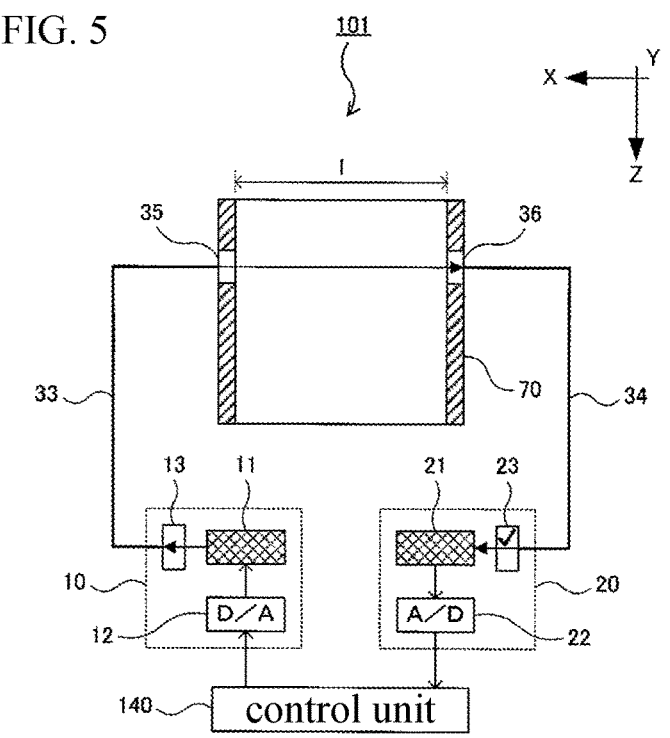
FIG. 5 is a schematic configuration drawing showing an example of a gas analyzer using wavelength tunable semiconductor laser absorption spectroscopy.
Figure 6A:
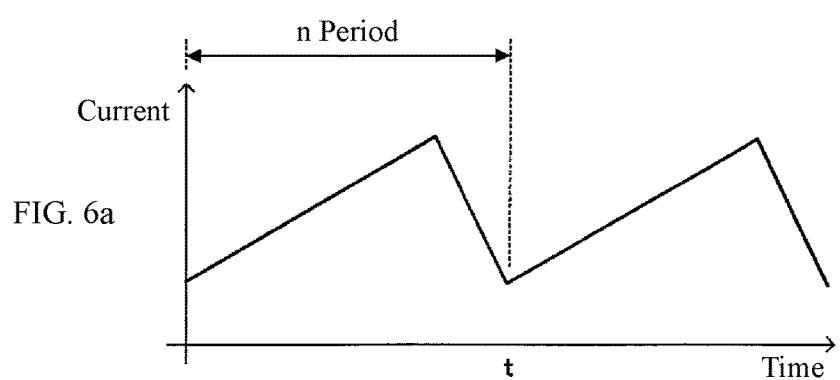
FIGS. 6a and 6b are conceptual drawings showing relationships between a drive current value and an oscillation wavelength of a laser beam, respectively.
Figure 6B:
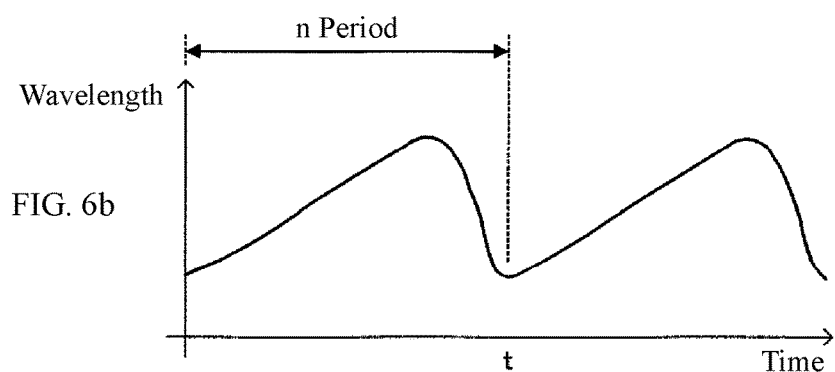

Also, with respect to the time-changing, $I_{vA}(t)$, of the light intensity at the wavelength vA, a fitting process is performed using a quadratic function in the fitting range W1 over the time zone t1, and a fitting process is performed using a quadratic function in the fitting range W2 over the time zone t2, and in that manner, the fitting process is performed using each quadratic function in each fitting range W over each time zone t. Thus, time-changing $i_{vA}(t)$ of the corrected light intensity is created. FIG. 3 is a graph in which an example (dashed line) of the time-changing $i_{vA}(t)$ of the corrected light intensity at the wavelength vA is superimposed on the graph of FIG. 2.

In this way, over the time zone in which the amount of gas pressure change ΔP(t) is small, the fitting process is performed with the time-changing $I_v(t)$ of the fitting range W over a long time interval, while the time zone in which the amount of gas pressure change ΔP(t) is large, the fitting process is performed with the time-changing $I_v(t)$ of the fitting range W over a short time interval, so that the time-changing $i_v(t)$ of the corrected light intensity at each wavelength v in the predetermined wavelength range of v1 to v2 is created.

The calculation unit 41g creates an intensity change $i_{On}(v)$ by creating an approximate expression based on the intensity $i_n(v)$ of the laser light of the non-absorptive wavelength in each cycle n, and performs control to calculate the number density Cn of n cycles using equation (1).

As described above, according to the gas analyzer 1 of the present invention, by setting the fitting range, W, and by using the amount of gas pressure change ΔP(t) for counting, the fitting range W related to the periodic change by the influence of the interference noise can be appropriately selected. As a result, the number density Cn can be accurately calculated in the measurement target gas in which the pressure P changes greatly.

OTHER EMBODIMENTS (1) In the gas analyzer 1 described above, the light source section 10 is provided with the DFB semiconductor laser diode 11, but it can also be a configuration with having a short wavelength laser, a white light source, a super luminescent diode light source or the like.

(2) In the gas analyzer 1 described above, a configuration was indicated where the fitting range W is determined by substituting the amount of gas pressure change ΔP(t) into equation (2), but it is also possible to have a configuration that uses another method with a fitting range over a long time interval in a time zone where the amount of gas pressure change ΔP(t) is small, and with a fitting range over a short time interval in a time zone where the amount of gas pressure change ΔP(t) is large.

(3) In the gas analyzer 1 described above, the fitting process is performed using a quadratic function, but it is also possible to adopt a configuration in which the fitting process is performed using another method.

INDUSTRIAL APPLICABILITY

The present invention can be applied to a gas analyzer or the like for measuring information on specific gas amount in a gas.

EXPLANATION OF SIGN

1 Gas analyzer
10 Light source section
20 light receiving section
32 Pressure sensor
41 *a* laser controller
41 *d* gas pressure change amount calculation unit
41 *e* Acquisition signal creation unit
41 *f* correction signal creation unit
41 *g* calculation unit
50 Engine (Measurement object)

What is claimed is:

1. A gas analyzer comprising:
   a light source member for irradiating measurement light at predetermined time intervals in a predetermined wavelength range of v1 to v2 to a target gas for measurement in an object for measurement;
   a light receiving member for receiving a light intensity I of the measurement light having passed through the measurement target gas;
   a calculation member for calculating specific gas amount information in n cycles, using a light intensity change $I_n(v)$ of the measurement light in the predetermined wavelength range of v1 to v2 of the nth cycle;
   a pressure sensor for detecting a gas pressure P of the measurement target gas;
   a gas pressure change amount calculation member for generating a time-changing P(t) of the gas pressure P and for calculating an amount of gas pressure change ΔP(t) at each time t;
   an acquisition signal generating member for generating a time-changing $I_v(t)$ of the light intensity at each wavelength v; and
   a correction signal creation member for generating a time-changing $i_v(t)$ of a corrected light intensity at each wavelength v, by performing a fitting process using the time-changing $I_v(t)$ over a long time interval in a time zone in which the amount of gas pressure change ΔP(t) is small but using the time-changing $I_v(t)$ over a short time interval in a time zone in which the amount of gas pressure change ΔP(t) is large,
   wherein the calculation member generates a light intensity change $i_n(v)$ of the measurement light in the predetermined wavelength range of v1 to v2 of the nth cycle by using the time-changing $i_v(t)$ of the corrected light intensity at each wavelength v, and calculates the specified gas amount information for the nth cycle.

2. The gas analyzer according to claim 1, wherein the light source member comprises:
   a laser element; and
   a laser control member for oscillating the measurement light in the predetermined wavelength range v1 to v2 from the laser element at a constant period n.

3. The gas analyzer according to claim 2,
wherein the object to be measured includes an internal combustion engine that performs an intake step, a compression step, a combustion step, and an exhaust step in a predetermined cycle.

4. The gas analyzer according to claim 1,
wherein the object to be measured includes an internal combustion engine that performs an intake step, a compression step, a combustion step, and an exhaust step in a predetermined cycle.

* * * * *